(12) United States Patent
Allen et al.

(10) Patent No.: US 10,937,551 B2
(45) Date of Patent: *Mar. 2, 2021

(54) MEDICAL CONCEPT SORTING BASED ON MACHINE LEARNING OF ATTRIBUTE VALUE DIFFERENTIATION

(71) Applicant: International Business Machines Corporation, Armonk, NY (US)

(72) Inventors: Corville O. Allen, Morrisville, NC (US); Roberto DeLima, Apex, NC (US); Aysu Ezen Can, Cary, NC (US); Robert C. Sizemore, Fuquay-Varina, NC (US)

(73) Assignee: International Business Machines Corporation, Armonk, NY (US)

( * ) Notice: Subject to any disclaimer, the term of this patent is extended or adjusted under 35 U.S.C. 154(b) by 338 days.

This patent is subject to a terminal disclaimer.

(21) Appl. No.: 15/822,651

(22) Filed: Nov. 27, 2017

(65) Prior Publication Data

US 2019/0163875 A1    May 30, 2019

(51) Int. Cl.
*G16H 50/70*     (2018.01)
*G16H 50/20*     (2018.01)
*G06F 40/295*    (2020.01)

(52) U.S. Cl.
CPC ........... *G16H 50/70* (2018.01); *G06F 40/295* (2020.01); *G16H 50/20* (2018.01)

(58) Field of Classification Search
CPC ....... G16H 50/70; G16H 50/20; G06F 40/295
See application file for complete search history.

(56) References Cited

U.S. PATENT DOCUMENTS 8,015,136 B1 * 9/2011 Baker .................... G16H 50/30
706/45
8,275,803 B2    9/2012 Brown et al.
(Continued)

FOREIGN PATENT DOCUMENTS

CN    102483818 A    5/2012

OTHER PUBLICATIONS

Mona Nagy ElBedwehy, et al.; "Computational Model for Artificial Learning Using Formal Concept Analysis", 2013, IEEE, 978-1-4799-0800-0/13, pp. 9-14 (Year: 2013).*
(Continued)

*Primary Examiner* — Evangeline Barr
(74) *Attorney, Agent, or Firm* — Stephen J. Walder, Jr.; Reza Sarbakhsh

(57) ABSTRACT

Mechanisms are provided for performing entity differentiation. A cognitive medical system ingests a corpus of medical content having references to medical entities, and performs entity recognition on the medical content to identify the medical entities. Responsive to the cognitive medical system identifying a medical entity having a plurality of annotations for a same medical entity attribute, an entity differentiation component executes an ordered set of entity differentiation algorithms, corresponding to the medical entity, for differentiating medical entity attribute values. The entity differentiation component runs the ordered set of entity differentiation algorithms, in order, on the plurality of annotations for the attribute to generate a ranked list of medical entity attribute values corresponding to the annotations in the plurality of annotations. The cognitive medical system performs a cognitive operation on the medical entity based on the ranked list of medical entity attribute values.

18 Claims, 6 Drawing Sheets

(56) References Cited

U.S. PATENT DOCUMENTS

| | | | |
|---|---|---|---|
| 8,548,937 B2 | 10/2013 | Saigal et al. | |
| 9,460,400 B2 | 10/2016 | De Bruin et al. | |
| 2005/0203930 A1* | 9/2005 | Bukowski | G06F 16/29 |
| 2009/0287678 A1 | 11/2009 | Brown et al. | |
| 2010/0145734 A1 | 6/2010 | Becerra et al. | |
| 2011/0066587 A1 | 3/2011 | Ferrucci et al. | |
| 2011/0125734 A1 | 5/2011 | Duboue et al. | |
| 2012/0078062 A1 | 3/2012 | Bagchi et al. | |
| 2013/0007055 A1 | 1/2013 | Brown et al. | |
| 2013/0018652 A1 | 1/2013 | Ferrucci et al. | |
| 2013/0019286 A1 | 1/2013 | Barborak et al. | |
| 2013/0033008 A1 | 2/2013 | Martin et al. | |
| 2013/0066886 A1 | 3/2013 | Bagchi et al. | |
| 2013/0332187 A1 | 12/2013 | Maman et al. | |
| 2014/0095186 A1 | 4/2014 | Gotz et al. | |
| 2014/0136230 A1 | 5/2014 | Berdia | |
| 2014/0142962 A1 | 5/2014 | Bhatt et al. | |
| 2014/0143881 A1 | 5/2014 | Boday et al. | |
| 2014/0188462 A1 | 7/2014 | Zadeh | |
| 2014/0201126 A1 | 7/2014 | Zadeh et al. | |
| 2014/0280112 A1 | 9/2014 | Cheng et al. | |
| 2014/0365232 A1 | 12/2014 | Sadeghi | |
| 2015/0193583 A1 | 7/2015 | McNair et al. | |
| 2015/0234987 A1 | 8/2015 | Laing et al. | |
| 2015/0363559 A1 | 12/2015 | Jackson et al. | |
| 2016/0004829 A1 | 1/2016 | Beqaj | |
| 2016/0062982 A1 | 3/2016 | Wroczynski et al. | |
| 2016/0140318 A1 | 5/2016 | Stangel | |
| 2016/0188535 A1 | 6/2016 | Allen et al. | |
| 2016/0259899 A1 | 9/2016 | Ludviksson et al. | |
| 2016/0328526 A1 | 11/2016 | Park et al. | |
| 2016/0364544 A1 | 12/2016 | Das et al. | |

OTHER PUBLICATIONS

List of IBM Patents or Patent Applications Treated as Related, Feb. 23, 2018, 2 pages.

List of IBM Patents or Patent Applications Treated as Related, Nov. 27, 2017, 2 pages.

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.

Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.

High, Rob, "The Era of Cognitive Systems: An Inside Look at IBM Watson and How it Works", IBM Corporation, Redbooks, Dec. 12, 2012, 16 pages.

Jacquelinet, Christian, "A Void Type for Medical Language Disambiguation", Springer-Verlag Berlin Heidelberg, International Conference on Conceptual Structures, Jul. 19, 2004, pp. 142-155.

Kaushik, Saurav, "Introduction to Feature Selection methods with an example (or how to select the right variables?)", Analytics Vidhya, https://www.analyticsvidhya.com/blog/2016/12/introduction-to-feature-selection-methods-with-an-example-or-how-to-select-the-right-variables/, Dec. 1, 2016, 32 pages.

Kremer, Ingrid E. et al., "Identification and Prioritization of Important Attributes of Disease-Modifying Drugs in Decision Making among Patients with Multiple Sclerosis: A Nominal Group Technique and Best-Worst Scaling", PLoS One, https://www.ncbi.nlm.nih.gov/pubmed/27812117, Nov. 3, 2016, 16 pages.

Lutfey, Karen E. et al., ""How are patient characteristics relevant for physicians' clinical decision making in diabetes?: An analysis of qualitative results from a cross-national factorial experiment"", National Institutes of Health, Author Manuscript, Soc Sci Med., vol. 67, No. 9, Nov. 2008, pp. 1391-1399.

Mccord, M.C. et al., "Deep parsing in Watson", IBM J. Res. & Dev. vol. 56 No. 3/4 Paper 3, May/Jul. 2012, pp. 3:1-3:15.

Rebholz-Schuhmann, Dietrich et al., "Annotation and Disambiguation of Semantic Types in Biomedical Text: a Cascaded Approach to Named Entity Recognition", NLPXML '06 Proceedings of the 5th Workshop on NLP and XML: Multi-Dimensional Markup in Natural Language Processing, Apr. 4, 2006, pp. 11-18.

Smith, Megan et al., "Factors influencing clinical decision making", Elsevier Health Sciences, Clinical Reasoning and Clinical Decision Making—Nature and Context, Clinical Reasoning in the Health Professions, Third Edition, Chapter 8, Feb. 18, 2008, pp. 89-100.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

Zhang, Yaoyun et al., "Chemical named entity recognition in patents by domain knowledge and unsupervised feature learning", Database, Apr. 17, 2010, 10 pages.

* cited by examiner

MEDICAL CONCEPT SORTING BASED ON MACHINE LEARNING OF ATTRIBUTE VALUE DIFFERENTIATION

BACKGROUND

The present application relates generally to an improved data processing apparatus and method and more specifically to mechanisms for performing medical concept sorting based on machine learning of attribute value differentiation.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions which are executed by the at least one processor and configure the at least one processor to implement a cognitive medical system and an entity differentiation component. The method comprises ingesting, by the cognitive medical system, a corpus of medical content, wherein the medical content comprises references to medical entities. Ingesting the corpus comprises performing entity recognition on the medical content to identify the medical entities. The method further comprises, responsive to the cognitive medical system identifying a medical entity having a plurality of annotations for a same medical entity attribute, determining, by the entity differentiation component executing in the data processing system, an ordered set of entity differentiation algorithms, corresponding to the medical entity, for differentiating medical entity attribute values. Moreover, the method comprises running, by the entity differentiation component, the ordered set of entity differentiation algorithms, in order, on the plurality of annotations for the attribute to generate a ranked list of medical entity attribute values corresponding to the annotations in the plurality of annotations. In addition, the method comprises performing, by the cognitive medical system, a cognitive operation on the medical entity based on the ranked list of medical entity attribute values.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5 depicts entity differentiation including choosing algorithms based on goal in accordance with an illustrative embodiment;

DETAILED DESCRIPTION

Figure 1:
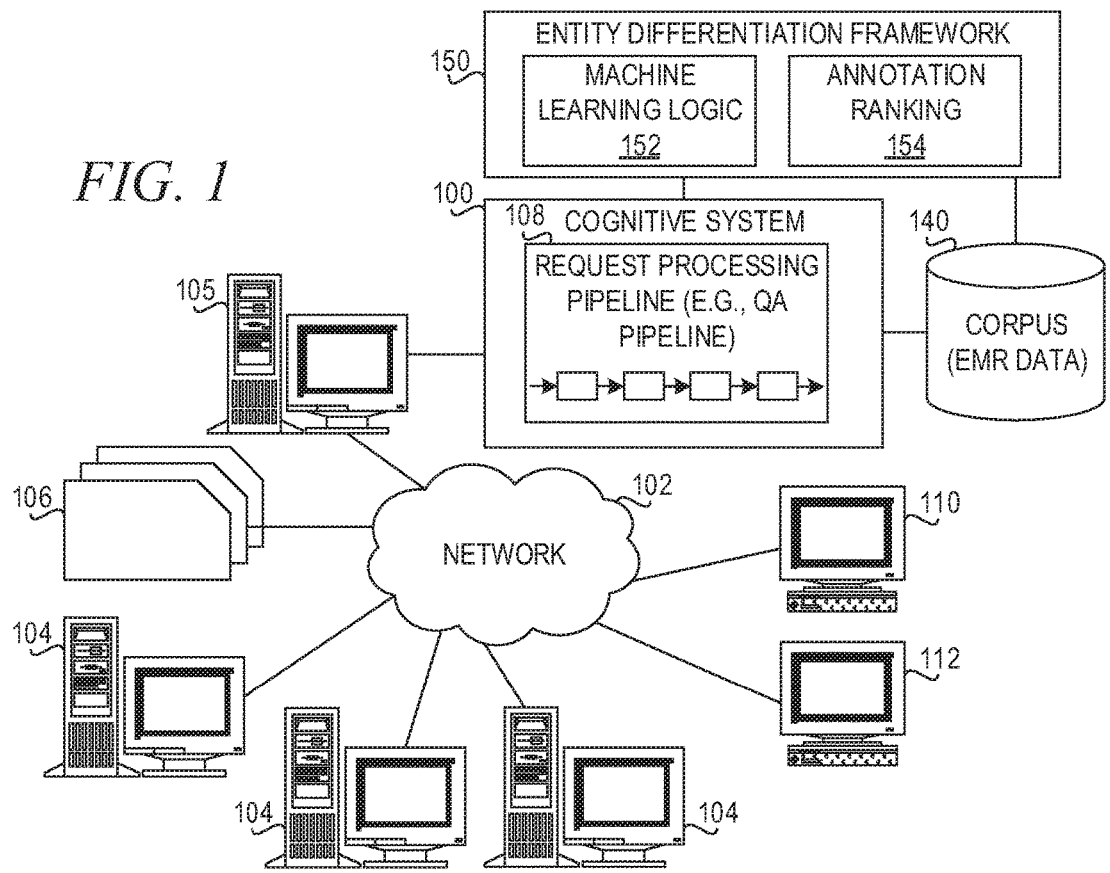
FIG. 1 depicts a schematic diagram of one illustrative embodiment of a cognitive system in a computer network.

Medical text contains a large number of concepts that are important to be extracted to derive inferences and make intelligent decisions in an automated manner. Most of the time, an electronic medical record (EMR) is composed of histories of illnesses, multiple observations (varying by date, size, examination type, etc.) and annotations. Physicians can easily decide which annotations are important for an overall decision; however, this is a difficult process for a cognitive system, such as a clinical decision support system, because the heuristics that physicians acquire over time and through experience are not present in computerized systems. That is one of the main reasons that physicians can come up with a primary treatment in their minds while algorithms must choose among a plurality of treatments based on rigid rule sets, often with difficulty in differentiating treatments based on the patient.

For instance, in an oncology clinic, the way physicians determine the most important tumor size differs based on the cancer type. If the patient has lung cancer, the tumor sizes in the lung are important and are regarded as primary. If the patient has breast cancer, physical examination results play an important role as well. Therefore, to be able to imitate the level of specificity based on the disease, current state of the art requires rewriting medical logic for each disease, which is time consuming and labor intensive. To be able to write specific medial logic, one must understand the disease and be able to draw conclusions based on attributes. In order to be able to facilitate this process, it is crucial to universalize the process of differentiating concept values (e.g., current latest, report type, modality) based on disease (e.g., lung cancer) and attribute type (e.g., tumor size). Such universalization framework should be able to differentiate concept values that are more important (e.g., tumor size in lung rather than in breast) and surface those to be used in the business goal (e.g., treatment recommendation, clinical trials matching, etc.).

The illustrative embodiments provide a mechanism for performing attribute value differentiation for text using machine learning. While the following description will demonstrate embodiments applied to the healthcare industry with specific reference to attribute values found in healthcare related natural language document data structures, it should be appreciated that the mechanisms of the illustrative embodiments are applicable to any domain and any industry in which attribute values are found in natural language text, such as in the financial industry, or the like.

In medical text, especially patient notes (also referred to as clinician notes or case notes) in electronic medical records (EMRs), where there are multiple reports documented in the patient notes, it is typical to see multiple occurrences of a medical concept, e.g., tumor size. An important challenge in automatically processing medical text by natural language processing systems, cognitive computing systems, and the like that operate on natural language text, is to select which attribute values associated with a concept should be used among a list of attribute values to identify which instances of a concept, i.e. concept values, are to be used to perform cognitive operations, such as treatment recommendations, clinical trial matching, etc. For example, when a cognitive system is attempting to generate treatment recommendations for use by a clinician when treating a patient, the cognitive system may need to annotate the tumor size instances (entities) found in the natural language text of the patient EMR using natural language processing algorithms, and then select the most reliable tumor size annotation from the list. That is, all instances of tumor sizes may be annotated, but only one of those annotations may correspond to the most reliable attribute value for the concept of a tumor size.

For example, there may be multiple different tests given to the patient that may specify different sizes for the same tumor due to the different modalities of imaging or other factors. If a reliable tumor size annotation is not selected, a conflict may be flagged for the patient case, e.g., different treatment recommendations may be generated based on different tumor size values associated with the different annotations, which then needs to be resolved by the clinicians to be able to continue with treatment recommendation generation by the cognitive system. This generally slows down the cognitive operations being performed by the cognitive system. Therefore, it is crucial to be able to select the most reliable annotations specifying a correct attribute value for each concept identified by the natural language processing. For example, between four different annotations in natural language content for a particular tumor's size, it is important to select the most reliable one of these four annotations for use in determining treatment recommendations for the patient rather than determining treatment recommendations for all four and requiring a human clinician to resolve the conflict.

It should be appreciated that the annotation is a portion of metadata identifying a concept type of an element of natural language text, e.g., medical concept, with one or more corresponding attributes and attribute value types, e.g., the annotation may be tumor:tumorsize:measurement, where "tumor" is the medical concept, "tumorsize" is the attribute, and "measurement" is the attribute value type. The actual value corresponding to the attribute value type may be extracted from the natural language content itself, e.g., 4 cm. Various formats of annotations may be used depending on the desired implementation, but in general will specify characteristics of the natural language elements found in natural language content by application of annotators, i.e. algorithms specifically trained and configured to identify particular types of natural language elements in natural language content and generate corresponding annotations.

As another example that illustrates the need to be able to accurately select the most reliable concept value, consider the selection of a value for the Metastatic Category (or MCategory) entity, where the MCategory entity categorizes cancer according to distant metastasis (M), Melanoma. When a patient EMR sets forth a series of clinician notes that reference the MCategory of the patient, the MCategory may be initially unknown, e.g., may be specified as "Mx", but later may be determined to be a particular category value (attribute value), i.e. a MCategory of "M0" or "M1". It is important to be able to use the MCategory that is the most recent, most reliable, and most accurate. For the overall treatment recommendation being generated by the cognitive system, it is crucial to know whether the patient is metastatic or not since this will change the nature of the treatment that will be recommended for treating the patient.

The illustrative embodiments provide mechanisms for performing machine learning based on the cognitive operations of a cognitive system implementing one or more medical logic algorithms that operate to determine the selection of annotations and their corresponding concepts, attributes, and attribute values. These medical logic algorithms select annotations corresponding to concepts having attributes and corresponding attribute values, based on their priorities. The priorities of the attributes are determined based on multiple criteria such as modalities, prior surgeries, and other factors that may be specific to the particular patient. The machine learning mechanisms of the illustrative embodiments learn which algorithms, and the order of algorithms, that determined the annotations and their set of concepts, attributes, and attribute values, and which set of algorithms and order of algorithms were used to determine a preferred attribute value for the concept. Based on the learned set and order of algorithms used to identify the preferred attribute and attribute value, the illustrative embodiments may apply this set and order of algorithms to find annotations associated with preferred attributes and attribute values when applied to other medical conditions, diseases, abnormalities, or the like, that may be added to the cognitive system, as well as additional medical concepts considered by the cognitive system, via the inclusion of additional logic added to the cognitive system following training of the cognitive system.

In some cases, the ordering of algorithms applied for identifying values for attributes/concepts defined for a particular disease or medical condition may be dynamically modified, or modified at the time of implementation of the disease or medical condition associated logic in the cognitive system. These modifications may be based on the identified set and order of algorithms learned to provide the preferred values for the attributes. That is, as will be described hereafter, through clustering of attributes across cases (patient EMR collections), a closest cluster may be identified to a new disease or medical condition's attributes so that corresponding algorithms and orders of algorithms for the closest cluster may be utilized to select annotations for the new disease or medical condition's logic for evaluation. Further training and tuning of the cognitive system may be required thereafter depending on the performance of the cognitive system for the new disease or medical condition, as may be performed using machine learning based on user feedback, however the clustering approach provides a high-performance baseline from which this additional training and tuning may be performed.

As an example, a portion of natural language text in a patient EMR, such as one or more case notes, may be ingested by a cognitive system, such as the IBM Watson™ cognitive system available from International Business Machines (IBM) Corporation of Armonk, N.Y., and may reference a medical concept, such as a tumor size or creatinine clearance level, which is then used to identify appropriate responses and treatments. Some medical concepts in the case notes may have multiple values. For example, during a course of treatment, a tumor may be measured multiple times on different days using a variety of procedures, such as via an ultrasound or mammogram, at different labs, and may even be measured after successful treatment to reduce/remove the tumor, all of which could result in varying measurements reflected in case notes in the patient EMR. For example, a case note may contain an entry indicating that an ultrasound measured a tumor at 3.1 cm. The same, or a different, case note may also indicate that a mammogram measured the tumor at 4 cm. Further, the case note may indicate that the ultrasound measurement is more recent and occurred after treatment. Thus, the case note includes the concept of a tumor size with two values, 3.1 cm and 4 cm, as well as attributes for each value, i.e. timing of the value, whether the value was before or after treatment, etc. The attributes are related to how the values were determined, the ultrasound and mammogram, as well as the dates the values were determined.

In general, the term "attributes" refers to the set of concrete clinical attributes that are used to drive medical application logic. An "attribute" is typically a singleton that represents a concept type and the final conclusion in the form of a normalized value. A "concept" is simply an abstract categorization of semantic meaning. For example, "tumor size" is a concept, and its realization in an electronic document, EMR, or the like, is an attribute. The mechanisms of the illustrative embodiments determine an attribute value from the evidence presented in structured content and unstructured natural language content. The evidence for an attribute is made up of one or more instances of normalized annotated mentions (sometimes referred to as entities). These mentions are also manifestations of a given concept.

The cognitive system operates to evaluate the case note, to select candidate attribute values for processing, select an attribute value for a concept from the patient data, process the concepts and ultimately recommend a treatment. To do so, the cognitive system determines which attributes and their attribute values are preferred attributes for evaluating the concept. That is, it is preferable that the "best" instance of the attributes (instantiations of a concept) present in the case note(s) be used to evaluate the case note(s), where the case note(s) may be provided in one or more electronic medical records (EMRs) associated with a patient obtained from the same or different EMR sources, such as hospitals, medical laboratories, physician offices, or other sources of EMR data. Thus, the cognitive system needs to identify which instance of a concept and its corresponding attribute and attribute value to use when generating a treatment recommendation.

For concepts of a same type, such as a measurement concepts for example, represented as annotations, the cognitive system selects candidate attribute values to use through implementation of an analysis "pipeline" as a part of the cognitive system. A typical pipeline may begin with request analysis, which analyzes (e.g., via natural language processing) and annotates the case note, using one or more annotators, to identify key concepts upon which a search of a corpus of electronic documents may be conducted. In addition, the system may identify candidate values of attributes, e.g., instantiations of the key concepts in the case note, especially in cases where there may be multiple candidate attribute values, such as in the tumor size measurements example above, for example "tumor size" is both a concept and an attribute, whereas "3 mm" is a candidate attribute value. The pipeline may then evaluate the attributes (concepts) and candidate attribute values from the case note using a trained cognitive model to determine a confidence score for the attribute values. The pipeline may then select an attribute value from the candidate attribute values, which may then be presented to the user via one or more user interfaces. The user interfaces may also include elements which allow the user to correct or modify the selected value. A pipeline may represent the execution of various analysis programs, or engines, on both the natural language content of the patient EMR, e.g., case note text, and a corpus of natural language, and possibly structured or semi-structured, text passages extracted from electronically stored documents from which candidate answers are generated, in order to deduce a probable correct answer.

Pipelines, or cognitive system pipelines, may be created for each domain or problem space, e.g., a different pipeline used for supporting treatment for different medical conditions. In fact, analysis engines themselves may be unique to a particular domain, e.g., different analysis engines for identification of a tumor stage or size, identification of drugs, potential drug interactions, etc. Content analysis engines within a pipeline may also include complex natural language processing algorithms, used, for example, to identify deep semantic relationships within the text. The scoring phase of cognitive system pipeline may also call various scoring algorithms to help determine a correct response or answer to a request. A scoring algorithm may generate one or more feature scores to indicate how confident it is in its response or answer. The cognitive system may also use a training phase to learn which features (attributes), or combinations of features (attributes), are best at predicting the right responses or answers for different types of requests, e.g., the attributes that are indicative of identifying a correct candidate attribute value for evaluating an instance of a medical concept. These features may be weighted more highly than other features when scoring the features of the candidate responses. Once the cognitive system has been trained, subsequent requests presented to the pipeline may use the machine learned model, i.e. combination of algorithms, to generate most likely correct responses or answers. It should be appreciated that such learning may be implemented for a plurality of different medical concepts and/or medical concept values.

The above outlined cognitive system based mechanism provides an intelligent system for determining the preferred attribute values for evaluating instances of medical concepts based on training of the cognitive system to learn what attributes of the medical concepts and corresponding attribute values associated with the medical concepts are indicative of correct attribute values for evaluating the medical concept, e.g., more often a timing of the test used to report a tumor size may be more indicative of a correct tumor size for evaluating a particular cancer type. This information may then be used to process, via a cognitive processing by the trained cognitive system, requests based on patient EMR data and a corpus of supportive documentation. For example, having determined what are the key attributes for evaluating a medical concept, when evaluating a new patient's EMR in which multiple instances of a same medical concept are present, the learned key attributes may be used to evaluate the new patient's EMR and identify which instance of the medical concept to utilize in performing a cognitive operation on the patient's EMR data, e.g., generating a treatment recommendation, evaluating the patient for inclusion in a medical trial, or the like.

In addition to, or as part of, the corpus of documentation, knowledge bases may be utilized to provide knowledge about medical concepts, e.g., diseases, treatments, etc., which may be used and leveraged by the cognitive system when performing its cognitive functions. For example, in the medical domain, these knowledge bases may have data structures that define various diseases including a specification of the important clinical attributes for that disease, e.g., tumor size, MCategory, patient age, patient gender, etc. This information may be used to score the attributes when performing training of the cognitive system by weighting attributes more highly when the knowledge base indicates the attribute to be of relatively higher importance to a disease or other medical concept.

The mechanisms of the illustrative embodiments include a framework and system for entity differentiation, where an entity is an instance of an attribute corresponding to a medical concept, where one important goal is to provide a capability to scale medical logic for more attributes and for more diseases as new diseases are defined in the cognitive system. This framework provides entity differentiation capabilities that automatically determines appropriate sets and ordering of algorithms to be applied when evaluating multiple instances of attributes and medical concepts (entities) in the natural language text of patient EMR data, such as textual passages that may be clinical notes or the like. Using this framework, attributes are ranked in order of relevance against all other attributes associated with a medical concept of the same type, in increasing accuracy with regard to their association with correct values for a medical concept. In addition, by customizing the logic for each medical concept, the illustrative embodiments make it possible to reflect the order of relevancy back to the user in a form where the user, e.g., clinicians and physicians in the case of a medical domain implementation, may provide feedback which can then be used through a machine learning approach to further train the framework, e.g., a cognitive system, to identify attributes indicative of correct values for a medical concept.

The mechanisms of the illustrative embodiments include logic implemented in a back-end request processing pipeline where natural language processing is performed. In the back-end request processing pipeline, after entity recognition is performed during an entity recognition phase, an entity differentiation operation is performed using an entity differentiation engine and its associated machine learning mechanisms in accordance with the illustrative embodiments. There may be many entities, but typically these will resolve to a single attribute, i.e. the conclusion of the entities. A concept is a term that equates to the semantic meaning of the entity, while the attribute value is the value of the given attribute or entity. Thus, for example, in a medical domain, the concept may be a tumor size while the "entity", i.e. an annotated instance of the concept or also referred to as an attribute, may be an instance of a tumor size in the patient's EMR. The attribute value of the concept may be a value of a tumor size, e.g., 4 cm. While this is an example in a medical domain, it should be appreciated that in other domains different types of concepts, entities, and values may be utilized that are specific to that domain for which the cognitive system of the illustrative embodiments is trained. The entity differentiation engine operates to select the preferred attributes and attribute values for machine learning to determine which attributes and attribute values are preferred based on the context surrounding the attribute value. The machine learning based model implemented by the entity differentiation engine may then be used to select from a ranked list of annotations, i.e. the entities, their attributes, and their values to drive the cognitive operation performed by the cognitive system, e.g., may provide the selected annotations and attribute values to drive a treatment recommendation performed by a cognitive treatment recommendation system.

Using a cognitive system for providing patient treatment recommendations as an example, during a training stage of operation, the machine learning aspects of the entity differentiation engine comprises, for each attribute A, that is used for a treatment recommendation, determining a set of criteria and algorithms for entity differentiation. The training of the cognitive system derives a conclusion about the value of a particular attribute. The evidence for that attribute/value may be some number of entities/annotations that pertain to the attribute.

In order to determine the set of criteria and algorithms, a set of annotations Ai_n, i.e the evidence, is determined. The set of annotations is the set of annotations that is used to derive the most preferred annotation, which is used as an attribute for the treatment recommendation. Machine learning is used to reverse engineer the process by which the preferred annotation is determined, i.e which algorithms were used to select Ai from Ai_n. Entities and cases (where a "case" is a collection of patient EMRs for a patient, for example) are grouped in the training set based on the annotation Ai selected from the set of annotation Ai_n, to thereby generate clusters of entities and cases. That is, a "cluster" refers to a collection of a given attribute across all cases. For example, if the attribute is "TumorSize", the cluster would be the evidence for TumorSize across all cases in the training set.

For each cluster C, a list of algorithms relevant for cases in the cluster C to differentiate attribute Aix, i.e. an instance of Ai for a given case/patient within the cluster C, is determined based on domain knowledge which may be present in one or more corpora. That is, domain knowledge in the one or more corpora may be processed, such as by using natural language processing or the like, to seed a list of criteria that is used to differentiate attributes of relevance to a concept. For example, it may be known from the domain knowledge that dates, modalities, and measurements are used by a medical professional when determining the primary tumor size. This knowledge may be used as a basis for identifying the algorithms that are implemented to differentiate attributes in the cluster C, e.g., algorithms directed to determining or which utilize dates, modalities, and measurements may be identified based on the domain knowledge so as to list the algorithms.

A set of pre-executed and post-execute algorithms relevant to the case for the cluster C is obtained, where pre-executed algorithms are the baseline set of algorithms used to establish a starting point and the post-execute algorithms are the algorithms that are used as part of the training process. The pre-executed algorithms and post-execute algorithms are predetermined based on data type and relative importance of the concept type, as well as subject matter expert input on what is an important for a medical concept. That is, the pre-executed algorithms are the starting set that was statically chosen based on empirical evidence and the post-executed algorithms refer to the sets that are tried as part of the training/testing process.

A set of output annotations related to entities and the associated attribute values is obtained. That is, for each attribute, a predetermined set of algorithms are applied and scored. These algorithms can be seen as conditions that differentiate attribute values. For example, a date algorithm that is looking for the most recent surgery would be applied of the surgery annotations, sorting them in a manner where the top entry shows the surgery that was conducted most recently. The scores obtained from these algorithms show the importance of this differentiation. For instance, the most recent surgery will have a higher score than the second most recent surgery, if their surgery types are the same. This allows medical logic to be able to understand the relative importance of each attribute value.

As the training process proceeds, different combinations and orders of these algorithms are applied and scored. After all of the various predetermined sets of algorithms are applied and scored for cluster C, final scores are computed for each predetermined set of algorithms applied, and the predetermined set of algorithms with the highest score is chosen. The scoring that was previously done was to sort attribute values. The final scoring orders attribute values based on the algorithms that were used for differentiating. For instance, the surgery type that was conducted can be of more importance than surgery date. Therefore, the surgery type algorithm will have a higher score than the surgery date. When the final sorting is done, the attribute values that were differentiated by the surgery type will have a higher score than the ones that used the date algorithm. The engine is trained by identifying the combinations of algorithms that most consistently result in the selection of an attribute value specified as the correct attribute value in a labeled dataset, also referred to as a golden dataset or ground truth dataset.

During a testing phase of operation, the output of the training phase, i.e. the set and order of algorithms to be applied for a given attribute, is used. During testing, the entity differentiation engine determines, for every case in the test set, and for every attribute Ai, a most suitable set and order of algorithms using the case as the criteria for the model learned during training. In order to choose the most suitable set and order of algorithms, a closest cluster for attribute Ai given all annotations in the case is found, e.g., the closest cluster may be the cluster associated with the specific attribute or a cluster that is associated with related attributes, for example breast primary tumor size versus liver primary tumor size. A patient that has breast cancer will need to be close to patients that have breast cancer. Therefore, a cluster that is associated with breast primary tumor size, rather than a cluster that is associated with lung primary tumor size, will give more accurate results. The related attributes for each cancer can be given while training the system or can be identified by the system using machine learning techniques, i.e., what are the attributes that help making a more accurate treatment recommendation for these set of patients. This can be addressed by a feature selection algorithm, such as chi-square or LDA for example, as described in Saurav Kaushik, "Introduction to Feature Selection methods with an Example (or how to select the right variables?)," Analytics Vidhya, December 2016, available at the Analytics Vidhya website.

The set and order of algorithms found for the cluster during training, i.e. the particular combination of algorithms that result in the correct attribute value, are then used to generate annotations for the case. A merge sort operation is executed on the annotations to percolate annotations that are higher priority to the top of the list of annotations. The ranked listing of annotations, from higher to lower priority, for attribute Ai is obtained from the results of the merge sort operation.

During a use phase of operation, the entity differentiation engine utilizes the highest ranked annotation to differentiate the value used for an attribute, i.e. determine the correct value for an attribute from a plurality of instances of values for the attribute in case notes of one or more patient EMRs or other patient information. For example, if a tumor size attribute is specified in a patient EMR in multiple instances, the entity differentiation engine selects an appropriate value that is the most accurate value based on annotations associated with the instances of the tumor size values and the highest ranked annotation from the training/testing phases, i.e. a value whose annotation matches the highest ranked annotation is selected.

The selected entity (attribute) and value are then used by the cognitive system to perform a cognitive operation, such as providing a treatment recommendation, evaluating the patient for a medical trial, or the like. That is, cognitive logic is applied using the selected entity and value as a correct entity/value for evaluating the cognitive logic. The results of the cognitive operation are then output to a clinician, or other medical personnel, to provide decision support services.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "component," if used herein with regard to describing embodiments and features of the invention, is not intended to be limiting of any particular implementation for accomplishing and/or performing the actions, steps, processes, etc., attributable to and/or performed by the component. A component may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular component is, unless otherwise specified, for purposes of convenience of reference and not intended to be limiting to a specific implementation. Additionally, any functionality attributed to a component may be equally performed by multiple components, incorporated into and/or combined with the functionality of another component of the same or different type, or distributed across one or more components of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
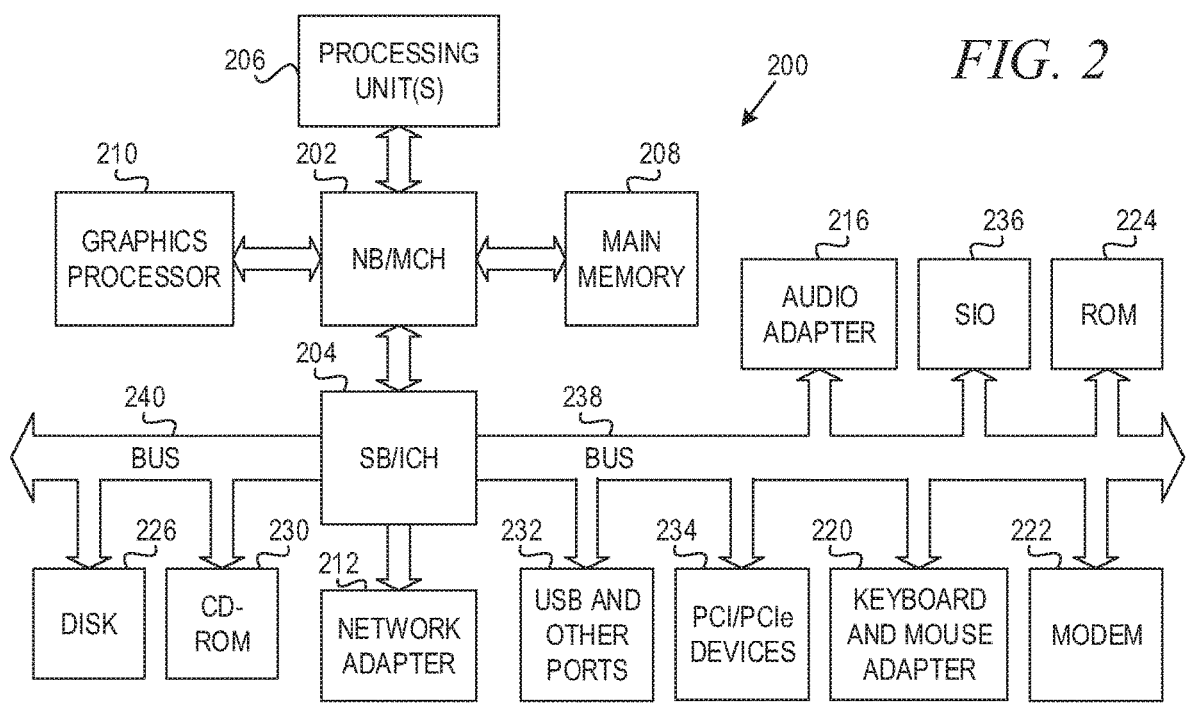
FIG. 2 is a block diagram of an example data processing system in which aspects of the illustrative embodiments are implemented.
Figure 3:
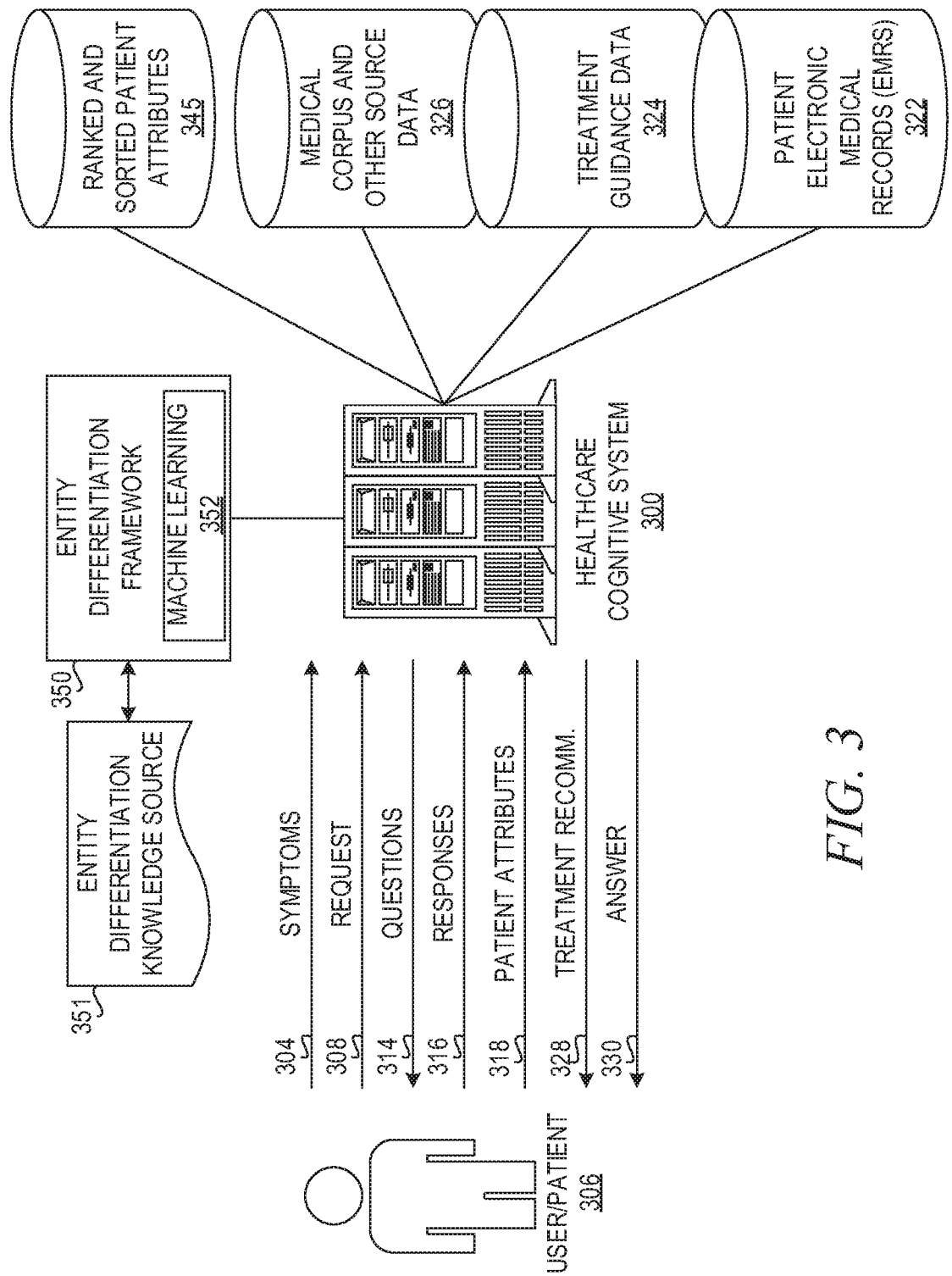
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a mechanism for verification of clinical hypothetical statements based on dynamic cluster analysis.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas, which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:
  Navigate the complexities of human language and understanding;
  Ingest and process vast amounts of structured and unstructured data;
  Generate and evaluate hypothesis;
  Weigh and evaluate responses that are based only on relevant evidence;
  Provide situation-specific advice, insights, and guidance;
  Improve knowledge and learn with each iteration and interaction through machine learning processes;
  Enable decision making at the point of impact (contextual guidance);
  Scale in proportion to the task;
  Extend and magnify human expertise and cognition;
  Identify resonating, human-like attributes and traits from natural language;
  Deduce various language specific or agnostic attributes from natural language;
  High degree of relevant recollection from data points (images, text, voice) (memorization and recall);
  Predict and sense with situational awareness that mimic human cognition based on experiences; and,
  Answer questions based on natural language and specific evidence.

FIG. 1 depicts a schematic diagram of one illustrative embodiment of a cognitive system 100 implementing a request processing pipeline 108, in a computer network 102. In one embodiment, the request processing pipeline 108 may be implemented as a question answering (QA) pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety.

The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables request processing for one or more cognitive system users via their respective computing devices 110-112. Other embodiments of the cognitive system 100 may be used with components, systems, sub-systems, and/or devices other than those that are depicted herein.

The cognitive system 100 is configured to implement a request processing pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and cognitive system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a request processing pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the request processing pipeline 108, which comprises a plurality of stages for processing an input question and the corpus of data 106. The request processing pipeline 108 generates answers for the input question based on the processing of the input question and the corpus of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a request processing pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The request processing pipeline of the IBM Watson™ cognitive system then performs deep analysis on the language of the request and the language used in each of the portions of the corpus of data found during the application of the queries using a variety of reasoning algorithms.

The scores obtained from the various reasoning algorithms are then weighted against a statistical model that summarizes a level of confidence that the request processing pipeline of the IBM Watson™ cognitive system has regarding the evidence that the potential response is inferred by the request. This process is repeated for each of the candidate responses to generate ranked listing of candidate responses, which may then be presented to the user that submitted the input request, or from which a final response is selected and presented to the user. More information about the request processing pipeline of the IBM Watson™ cognitive system may be obtained, for example, from the IBM Corporation website, IBM Redbooks, and the like. For example, information about the request processing pipeline of the IBM Watson™ cognitive system can be found in Yuan et al., "Watson™ and Healthcare," IBM developerWorks, 2011 and "The Era of Cognitive Systems: An Inside Look at IBM Watson™ and How it Works" by Rob High, IBM Redbooks, 2012.

As noted above, while the input to the cognitive system 100 from a client device may be posed in the form of a natural language question, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as the IBM Watson™ cognitive system, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the illustrative embodiments, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) 140 evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR 140 in relation to medical guidelines and other medical documentation in a corpus of information to generate a recommendation as to how to treat a medical malady or medical condition of the patient.

In accordance with an illustrative embodiment, the cognitive system 100 implements an entity differentiation framework 150 for entity differentiation where the primary goal is to scale medical logic for more attributes and for more diseases by making algorithm customization as simple as table updates. Entity differentiation framework 150 drives a set of medical logic based on metadata and on a goal, which allows the medical determination of relevance to be based on the goal for the concept and the entities. Framework 150 differentiates entity or concept impact by tying the medical logic algorithms to a set of attributes (e.g., modality, dates, document type, location, dimension, etc.) to drive concept differentiation dynamically. The entity differentiation framework 150 comprises machine learning logic 152 that identifies the algorithms used to identify the attributes and corresponding values associated with a correct value for a concept. The set and order of algorithms used to identify the attributes may be correlated with annotations of the patient EMR data which may be ranked according to relevance and the rankings may be stored in an annotation ranking data structure 154 for each medical concept. Based on the machine learning performed by the machine learning logic 152, the set and order of algorithms may be used to evaluate other patient EMR data with regard to instances of the medical concepts in the other patient EMR data and thereby identify attributes and attribute values to be utilized in cognitive logic when performing cognitive operations associated with the specified goal.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8°. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINTJX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient and/or user 306 as human figures, the interactions with and between these entities may be performed using computing devices, medical equipment, and/or the like, such that user/patient 306 may in fact be computing devices, e.g., client computing devices. For example, the interactions 304, 314, 316, and 330 between a patient and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a user/patient 306 presents symptoms 304 of a medical malady or condition to a healthcare cognitive system 300. The healthcare cognitive system 300 may interact with the user/patient 306 via a question 314 and response 316 exchange where the healthcare cognitive system 300 gathers more information about the patient, the symptoms 304, and the medical malady or condition of the patient. It should be appreciated that the questions/responses may in fact also represent the user 306 gathering information from the patient using various medical equipment, e.g., blood pressure monitors, thermometers, wearable health and activity monitoring devices associated with the patient such as a FitBit™ wearable device, a wearable heart monitor, or any other medical equipment that may monitor one or more medical characteristics of the patient. In some cases such medical equipment may be medical equipment typically used in hospitals or medical centers to monitor vital signs and medical conditions of patients that are present in hospital beds for observation or medical treatment.

In response, the user/patient 306 submits a request 308 to the healthcare cognitive system 300, such as via a user interface on a client computing device that is configured to allow users to submit requests to the healthcare cognitive system 300 in a format that the healthcare cognitive system 300 can parse and process in order to provide an answer 330. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 or answers 330 to the user/patient 306 to assist in treating the patient based on their reported symptoms 304 and other information gathered about the patient via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient to generate one or more treatment recommendation 328 or answers 330. The treatment recommendations 328 may be presented in a ranked ordering with associated supporting evidence, obtained from the patient attributes 318 and data sources 322-326, indicating the reasoning as to why the treatment recommendation 328 or answer 330 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients in a manner (structured, unstructured, or a mix of structured and unstructured formats) that the information may be retrieved and processed by the healthcare cognitive system 300. This patient information may comprise varied demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient is less than or equal to 60 years of age, has acute myeloid leukemia (AML), and no evidence of cardiac disease. Thus, for a patient that is 59 years of age, has AML, and does not have any evidence in their patient attributes 318 or patient EMRs indicating evidence of cardiac disease, the following conditions of the treatment rule exist:

Age <=60 years=59 (MET);
Patient has AML=AML (MET); and
Cardiac Disease=false (MET)

Since all of the criteria of the treatment rule are met by the specific information about this patient, then the treatment of Decitabine is a candidate treatment for consideration for this patient. However, if the patient had been 69 years old, the first criterion would not have been met and the Decitabine treatment would not be a candidate treatment for consideration for this patient. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient. The candidate treatment recommendations may then be ranked according to their confidence scores and presented to the user/patient 306 as a ranked listing of treatment recommendations 328. In some cases, only a highest ranked, or final answer, is returned as the treatment recommendation 328. The treatment recommendation 328 may be presented to the user/patient 306 in a manner that the underlying evidence evaluated by the healthcare cognitive system 300 may be accessible, such as via a drilldown interface, so that the user/patient 306 may identify the reasons why the treatment recommendation 328 is being provided by the healthcare cognitive system 300.

In accordance with the illustrative embodiments herein, the healthcare cognitive system 300 is augmented to operate with, implement, or include entity differentiation framework 350 for entity differentiation where the primary goal is to scale medical logic for more attributes and for more diseases by utilizing machine learning techniques to learn the most relevant annotations for evaluating a medical concept, where these annotations are associated with particular attributes and attribute values that are determined to be most relevant to the correct identification of a value of the medical concept. While the above description describes a general healthcare cognitive system 300 that may operate on specifically configured treatment recommendation rules, the mechanisms of the illustrative embodiments modify such operations to utilize the entity differentiation framework 350, which operates in the manner described below with particular reference to FIGS. 4-9.

For example, the operation of the entity differentiation framework 350 results in an identification of entities in the patient EMR data that is most relevant to the particular cognitive operation being performed by the healthcare cognitive system 300. For example, if the cognitive operation is to provide a treatment recommendation for a patient with regard to a particular cancer type, then the entity differentiation framework 350 provides functionality for selecting the appropriate entity in the patient EMR data 322 for performing such treatment recommendation, e.g., a most relevant tumor size entity based on a particular attribute and corresponding annotation, e.g., the most recently generated tumor size, or a tumor size generated from a particular type of imaging, modality, etc. It should be appreciated that a combination of different attributes may be evaluated in this manner such that a particular combination of attributes may be indicative of the most relevant annotation.

Thus, in response to the healthcare cognitive system 300 receiving the request 308 and patient attributes 318, the healthcare cognitive system 300 may retrieve the patient's EMR data from source(s) 322. This information is provided to entity differentiation framework 350, which differentiates annotations associated with attributes in the EMR data based on the machine learning performed by the machine learning logic 352 of the entity differentiation framework 350 and the resulting ranked listing of annotations and corresponding sets and order of algorithms used to generate such annotations, which may be stored in a data structure associated with an identifier of the medical concept 354.

Entity differentiation framework 350 references a set of entity differentiation knowledge sources 351 associated with a particular goal of the business logic, e.g., clinical trials matching or treatment recommendation. For a given attribute having a plurality of annotations of the same type, framework 350 performs machine learning, during a training phase, to learn the criteria, e.g., set and order of algorithms to execute, specific to the medical concept and attributes. The set of entity differentiation knowledge sources 351 identifies an ordered list of medical logic algorithms associated with the criteria for entity differentiation as learned through the machine learning performed by the machine learning logic 352.

For example, during a training stage of operation, the machine learning logic 352 of the entity differentiation engine 350 comprises, for each attribute A, that for which there are a plurality of annotations, determining a set of criteria and algorithms for entity differentiation. In order to determine the set of criteria and algorithms, a set of annotations $Ai\_n$ is determined. The set of annotations is the set of annotations that is used to derive the most preferred annotation Ai, which is used as a preferred attribute. Machine learning is used to reverse engineer the process by which the preferred annotation is determined, i.e which algorithms were used to select Ai from $Ai\_n$. Entities and cases (where a "case" is a collection of patient EMRs for a patient, for example) in a training set of cases are grouped, such as by clustering logic of the machine learning logic 352, based on the annotation Ai selected from the set of annotation $Ai\_n$, to thereby generate clusters of entities and cases. For each cluster C, a list of algorithms relevant for cases in the cluster C to differentiate attribute Aix, i.e. an instance of Ai for a given case/patient within the cluster C, is determined based on domain knowledge, such as may be provided in corpora 324-326 for example, which may be present in one or more corpora. That is, domain knowledge in the one or more corpora may be processed, such as by using natural language processing or the like, to seed a list of criteria that is used to differentiate attributes of relevance to a medical concept. This knowledge may be used as a basis for identifying the algorithms that are implemented to differentiate attributes in the cluster C, e.g., algorithms directed to determining or which utilize dates, modalities, and measurements may be identified based on the domain knowledge so as to list the algorithms.

Having identified a list of algorithms relevant to cases in the cluster C, a set of output annotations related to entities and the associated attribute values is obtained. That is, for each attribute, a predetermined set of algorithms are applied and scored. As the training process proceeds, different combinations and orders of these algorithms are applied and scored. After all of the various predetermined sets of algorithms are applied and scored for cluster C, final scores are computed for each predetermined set of algorithms applied, and the predetermined set of algorithms with the highest score is chosen. The entity differentiation framework 350 is trained by identifying the combinations of algorithms that most consistently result in the selection of an attribute value specified as the correct attribute value in a labeled dataset, also referred to as a golden dataset or ground truth dataset. The combinations of algorithms for the various attributes and/or medical concepts may then be stored in the entity differentiation knowledge source 351 for later use in evaluating other patient EMR data for patients based on the instances of attributes and medical concepts within the patient EMR data when performing a cognitive operation by the healthcare cognitive system 300.

During a testing phase of operation, the output of the training phase, i.e. the set and order of algorithms to be applied for a given attribute may be retrieved from the entity differentiation knowledge source 351 and used. During testing, the entity differentiation engine 350 determines, for every case in a test set, and for every attribute Ai, a most suitable set and order of algorithms using the case as the criteria for the model learned during training and stored in the entity differentiation knowledge source 351. In order to choose the most suitable set and order of algorithms, a closest cluster for attribute Ai given all annotations in the case is found, e.g., the closest cluster may be the cluster associated with the specific attribute or a cluster that is associated with related attributes The set and order of algorithms found for the cluster C during training, i.e. the particular combination of algorithms that result in the correct attribute value, are then used to generate annotations for the test case. A merge sort operation is executed on the annotations to percolate annotations that are higher priority to the top of the list of annotations. The ranked listing of annotations, from higher to lower priority, for attribute Ai is obtained from the results of the merge sort operation.

During a use phase of operation, the entity differentiation engine 350 utilizes the highest ranked annotation to differentiate the value used for an attribute, i.e. determine the correct value for an attribute from a plurality of instances of values for the attribute in case notes of one or more patient EMRs or other patient information. For example, if a tumor size attribute is specified in a patient EMR in multiple instances, the entity differentiation engine selects an appropriate value that is the most accurate value based on annotations associated with the instances of the tumor size values and the highest ranked annotation from the training/testing phases, i.e. a value whose annotation matches the highest ranked annotation is selected.

The selected entity (attribute) and value are then used by the healthcare cognitive system 300 to perform a cognitive operation, such as providing a treatment recommendation, evaluating the patient for a medical trial, or the like. That is, cognitive logic of the healthcare cognitive system 300, such as may be provided in the processing pipeline(s) of the healthcare cognitive system 300, is applied using the selected entity and value as a correct entity/value for evaluating the cognitive logic. The results of the cognitive operation are then output to the user 306, which may be a patient, a clinician, or other medical personnel, to provide decision support services.

While FIG. 3 is depicted with an interaction between the patient and a user, which may be a healthcare practitioner such as a physician, nurse, physician's assistant, lab technician, or any other healthcare worker, for example, the illustrative embodiments do not require such. Rather, the patient may interact directly with the healthcare cognitive system 300 without having to go through an interaction with the user and the user may interact with the healthcare cognitive system 300 without having to interact with the patient. For example, in the first case, the patient may be requesting 308 treatment recommendations 328 from the healthcare cognitive system 300 directly based on the symptoms 304 provided by the patient to the healthcare cognitive system 300. Moreover, the healthcare cognitive system 300 may actually have logic for automatically posing questions 314 to the patient and receiving responses 316 from the patient to assist with data collection for generating treatment recommendations 328. In the latter case, the user may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

Figure 4:
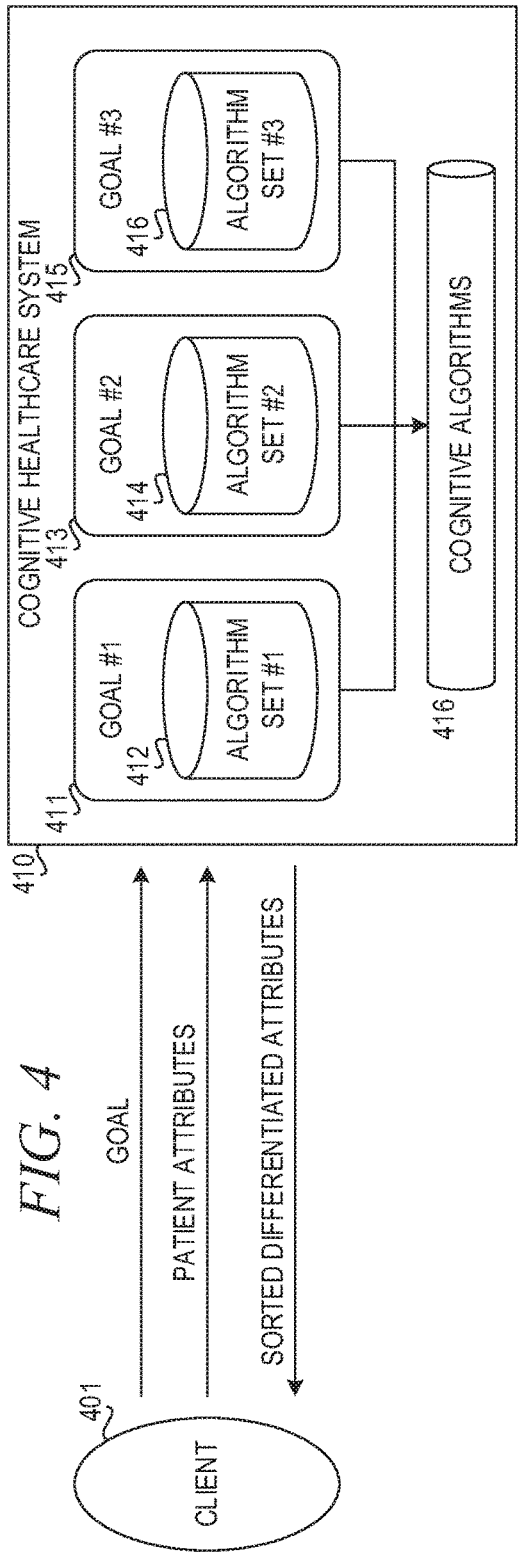
FIG. 4 is a block diagram illustrating an association of business goals with sets of cognitive algorithms in accordance with an illustrative embodiment.

FIG. 4 is a block diagram illustrating an association of business goals with sets of cognitive algorithms in accordance with an illustrative embodiment. Client 401 may be a patient or a user operating on behalf of the patient. Client 401 provides a goal and patient attributes to cognitive healthcare system 410. The goal identifies a business goal of the request from client 401, such as treatment recommendation, clinical trials matching, etc. Cognitive healthcare system 410 provides separate sets of algorithms for the different business goals, including goal #1 411 and algorithm set #1 412, goal #2 413 and algorithm set #2 414, and goal #3 415 and associated algorithm set #3 416. Each algorithm set 412, 414, and 416 provides a sorted list of algorithms to apply to the patient attributes to produce a set of sorted, differentiated attributes, referencing a store of cognitive algorithms 416.

A client 401 provides a set of patient attributes that are in natural language form or structured form for a desired goal of a cognitive healthcare system 410. The goals can be treatment recommendation, adverse event analysis, medical condition resolution, etc. Based on the goal, a set of entity differentiation knowledge sources are consulted to determine which algorithms from the set of algorithms would apply. Then, based on the set of algorithms, such as algorithm set #1 412, for example, that are executed in order, a sorted set of differentiated attributes are sent in response to the client 401.

The illustrative embodiments provide an elastic framework that scales to any number of diseases, settings, and attributes and learns for each combination of business goal, disease, settings, and attributes, which set and order of algorithms are preferred to select attributes and their corresponding annotations in natural language text for use in performing cognitive evaluations with regard to the particular business goal, disease, and settings. The learned set and order of algorithms for a particular business goal, disease, settings, and attributes may be used as default behavior that can be used as a baseline for extending the functionality of the cognitive healthcare system 410 to newly added diseases, medical conditions, or other medical concepts. Through clustering of annotations and concepts (e.g., diseases, medical conditions, or other medical concepts), and determining similarities between attributes of a new medical disease, condition, or concept with the attributes of the clusters, such as may be performed by clustering logic in the cognitive healthcare system 410, a learned set and order of algorithms used with a closest cluster of attributes/concepts may be applied to the newly added disease, medical condition, or other medical concept. This minimizes the amount of custom medical logic needed to write for a new disease or attribute. Thus, the entity differentiation framework 350 of the illustrative embodiments is a very effective way to scale medical interpretation logic by determining an appropriate set and order of algorithms to be used for newly added medical concepts, diseases, medical conditions, and the like.

FIG. 5 depicts entity differentiation including choosing algorithms based on goal in accordance with an illustrative embodiment. For a given disease the following important clinical attributes are defined in block 501:
  Tumor Size;
  Performance Status;
  Tcategory;
  Critical Disease Site (multi-valued attribute): brain met;
  Critical Disease Site: effusion;
  . . .

The business logic 502 is based on a goal (e.g., clinical trials matching or treatment recommendation) and a therapy history. The unstructured text 503 includes code for the various concepts or entities and a number of algorithms to be used. Algorithms are constructs that capture a specific set of logic to be performed during comparison of entity instances. Algorithms can be simple (e.g., comparing two values) or complex (e.g., comparing multiple values, considering contextual clues, etc.) and are generic enough that they can be reused for any number of stated goals or attributes. The exact algorithms used and the order in which they are invoked can be customized based on the needs of the application, and are intended to capture expert reasoning that is specific to the domain and attribute being differentiated. These algorithms and their order are learned by the machine learning logic of the illustrative embodiments as discussed previously.

Figure 6:
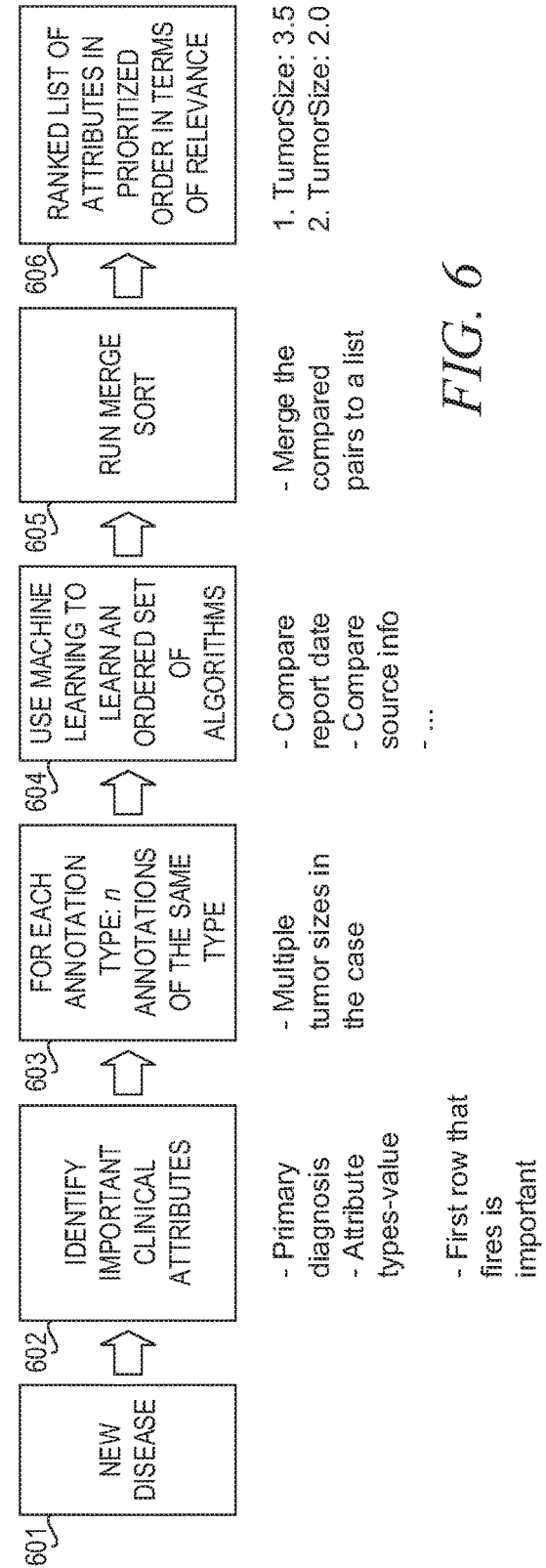
FIG. 6 is a block diagram illustrating an entity differentiation framework in accordance with an illustrative embodiment.

FIG. 6 is a block diagram illustrating an entity differentiation framework in accordance with an illustrative embodiment. In block 601 a new disease, medical condition, or medical concept is defined which includes a definition of the primary clinical attributes associated with that disease, medical condition, or medical concept. In block 602 the important clinical attributes for the new disease are identified, such as by analyzing the provided new disease definition and/or based on a learning of important clinical attributes, such as during a training operation. When a new disease is introduced, oftentimes the important clinical attributes are known by physicians, and are therefore provided to the system. However, when this knowledgebase is lacking, the important clinical attributes can be identified from the training set. Assume that the training set includes patient records, and their correct treatments. Once features are extracted from the electronical medical records, feature selection techniques are used to identify the important attributes for the given disease. For example, when the entities are detected such as tumor measurements, disease sites, the feature selection algorithms are used to determine that the tumor sizes are important for lung cancer, especially when they are in the lung which would make disease site of tumors important as well. In this way, the tumor location will be selected as an important attribute for lung cancer. An entity that identifies whether or not patient has smoked in the past can be extracted from electrical medical records. This information is useful for lung cancer cases and not useful for breast cancer. Therefore, smoking status is selected as an important attribute for lung cancer.

In block 603, the entity differentiation framework receives a number, n, of annotations of the same type. For example, these annotations may indicate multiple tumor sizes in a particular case. Thus, a given entity, concept, or attribute may have multiple annotations providing a value to the entity, concept, or attribute. In the above example, the entity is a tumor and the attribute is tumor size.

In block 604, the entity differentiation framework uses machine learning to determine the set of algorithms that are useful for the particular attribute for the given disease to a set of entity differentiation algorithms. For example, the entity differentiation framework may select a set and order of algorithms corresponding to the important clinical attributes of the new disease based on the machine learning used during training of the entity differentiation framework and which may be stored in an entity differentiation knowledge source. For the new disease, medical condition, or other medical concept, the important clinical attributes may be utilized to compare to the clusters identifying during training to select a closest cluster and the identify the set and order of algorithms associated with the closest cluster and apply that set and order of algorithms to the corresponding important attributes for the new disease, medical condition, or medical concept.

Thus, the entity differentiation framework executes the set of algorithms in order to compare pairs of annotations. In block 605, the entity differentiation framework runs a merge sort to merge the compared pairs to a list. A merge sort is an efficient, general-purpose, comparison-based sorting algorithm. Most implementations produce a stable sort, which means that the implementation preserves the input order of equal elements in the sorted output. Conceptually, a merge sort works as follows:
  1. Divide the unsorted list into sublists, each containing one element (a list of 1 element is considered sorted).
  2. Repeatedly merge sublists to produce new sorted sublists until there is only one sublist remaining. This will be the sorted list.

The merge sort from block 605 results in a ranked list of attributes in prioritized order in terms of relevance at block 606. In the previous example, the ranked list of attributes in block 606 for a patient EMR includes instances of tumor size of 3.5 cm and 2.0 cm, where 3.5 cm is a latest measured tumor size, such as after treatment, may be as follows: TumorSize=3.5, TumorSize=2.0, such that TumorSize=3.5 is given higher ranking than TumorSize=2.0.

The ranked listing of attributes from the patient EMR may then be provided back to the healthcare cognitive system which uses the highest ranked attribute and corresponding annotation as a basis for performing the cognitive operation associated with the business goal, e.g., treatment recommendation or the like. Thus, for purpose of treatment recommendation, for example, the cognitive logic may evaluate any references in the cognitive logic to a tumor size with the TumorSize=3.5 in the above example. Hence, multiple instances of the same attribute, and thus, multiple annotations for the same type of attribute, are differentiated and the most likely applicable instance of the attribute and annotation that will generate a correct evaluation of a corresponding medical concept, disease, or medical condition is selected and utilized.

Consider a use case for the attribute MCategory:MX, where the MCategory attribute again categorizes cancer according to distant metastasis (M), Melanoma. The categories are as follows:
  MX: Distant metastasis cannot be determined
  M0: No distant metastasis
  M1: Distant metastasis
  M1a: Metastasis to skin, subcutaneous tissues, or distant lymph nodes
  M1b: Metastasis to lung.

Stating notation expressed as M0, M1, M1a, M1b, and MX are all annotated by natural language processing (NLP). MX is always the least preferred value. In cases where stating notation is not present, the mechanism may derive MCateogry from presence of met sites or statements like "locally advanced" or "stage II." By doing the derivation over the span of the site or statement, the mechanism enables the differentiation framework to determine the MCategory attribute value to use.

An example algorithm, such as a NonPreferredValue algorithm, provides a means to treat certain values as less reliable. A comma-delimited list of ordered non-preferred values is passed in—in this case, the mechanism simply passes "MX" as a parameter. As instances of MCategory are processed, MX is pushed to the bottom of the heap, and M0, M1, M1a, M1b are sorted. The framework returns the desired answer.

Figure 7:
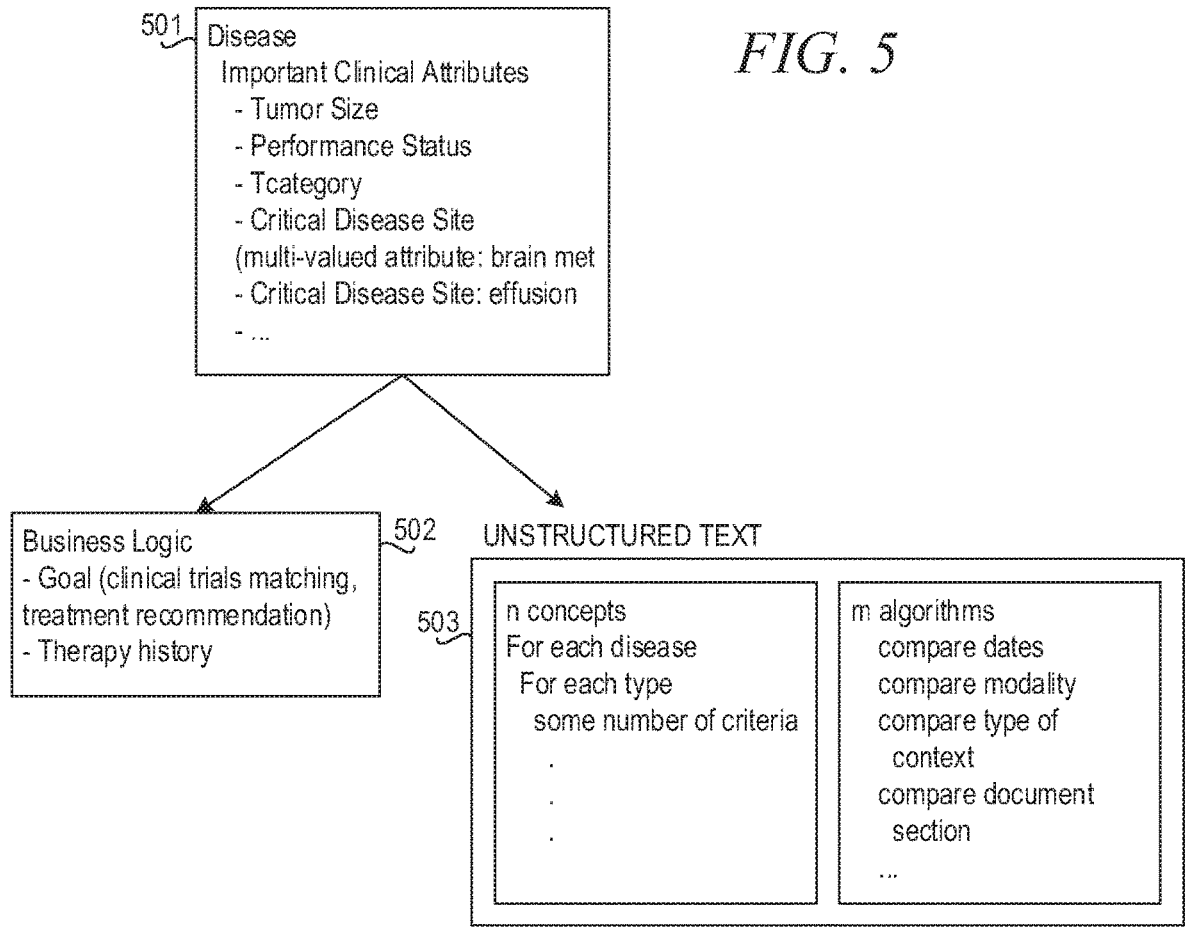
FIG. 7 depicts example entity differentiation table data structures for the MCategory attribute in accordance with an illustrative embodiment.

FIG. 7 depicts example entity differentiation algorithm sets and orders of algorithms that may be learned through machine learning of the illustrative embodiments for the MCategory attribute in accordance with an illustrative embodiment. The table shown in FIG. 7 may be a data structure generated by the machine learning of the illustrative embodiments based on a reverse engineering of the algorithms used to generate an annotation that is determined to represent the ground truth attribute value for MCategory during training. The machine learning, when learning the ordered set of entity differentiation algorithms to be used with a particular type of entity, e.g., medical entity, may determine and learn the implementation class and parameters associated with each entity differentiation algorithm in the ordered set of entity differentiation algorithms. These may then be used to execute the entity differentiation algorithms according to the determined order by calling the implementation class and passing the associated parameters. The table data structure as shown in FIG. 7, resulting from the determination of the ordered sets of entity differentiation algorithms, may be stored in an entity differentiation knowledge source for later retrieval and use when evaluating patient EMR data, e.g., calling of the implementation classes and passing of associated parameters.

As shown in FIG. 7, an entry in the table data structure for an attribute name of MCategory 701 is generated and stored by the machine learning logic of the illustrative embodiments, where the algorithm order is follows: StructuredAttributes, Confidence, MCatNonPreferredValue, SourceReport, ObservationDateMonths, ConclusiveAttribute, SourceInfoPriority, ObservationDate, ReportDate. The algorithm named MCatNonPreferredValue 702 has an entry associated with parameter MX 703. This parameter indicates that MX is the non-preferred value to be pushed to the bottom of the sort. Note that in this example MCatNonPreferredValue calls the NonPreferredValue implementation class with case-specific parameters.

Consider another use case for the attribute named PatientAge, as shown in FIG. 7. The highest value represents the oldest age at which a stating notation was made. A case may have multiple PatientAge annotations in multiple notes, as follows:

"The patient is a 44-year-old female who was recently diagnosed with . . . "

"NAME[CCC. BBB] is a 45-year-old premenopausal woman, status post a right total mastectomy . . . "

No logic results in a surface conflict for PatientAge. The mechanism may use medical logic or a generic algorithm that compares preferred values. The MaxPreferredValue algorithm is not specific to the concept. It is a generic algorithm that could be used for differentiating other attributes as well.

Consider another use case of differentiating tumor size (not shown in FIG. 7). A current approach of cancer-specific JRules requires new models for each cancer. The determination of the "correct" tumor size is always algorithmic and determines whether it is a primary site, the modality of observation, and size in the largest dimension. This decomposes into standard algorithms as follows:

LungPrimarySite is a parameterized instance of PrimarySite with sites considered local for lung cancer;

LungSourceInfoPriority is a parameterized instance of SourceInfoPriority with modalities relevant for determining lung tumors; and, MaxPreferredValue chooses the maximum size.

Additional cancers are easily implemented by determining the important attributes automatically and determining the correct order of algorithms using the clustering technique defined above eliminating the need for medical logic to differentiate each specific cancer. The algorithms in this example (e.g., LungPrimary Site, LungSourceInfoPriority, MaxPreferredValue) are determined with the help of machine learning algorithms for lung cancer. Furthermore, the order in which these algorithms are applied are also determined using machine learning models. The order in which these algorithms are applied can be changed by domain experts, however, they are determined automatically initially.

Thus, the illustrative embodiments provide a machine learning mechanism that allows the reuse of underlying algorithms that drive their relevance and output based on the best value for an annotation given a set of criteria constraints and a particular goal, e.g., the goal of the cognitive healthcare system utilizing the algorithms, e.g., treatment recommendation, adverse event analysis, medical condition resolution, medical trial candidacy evaluations and recommendations, or the like. For example, the illustrative embodiments may execute a set of algorithms for medical trial matching vs. treatment recommendation, versus therapy history analysis on a case, however the preferred attribute values and the order of the algorithms may be different for each business goal. Through the machine learning of the illustrative embodiments, the cognitive system may quickly determine the best attribute values and set/order of algorithms to use as the cognitive system transitions to similar domain based execution. The illustrative embodiments further allow for medical logic to scale rapidity since the machine learning permits the algorithms to be reused for new medical logic based on clustering and correlations of attributes of the medical logic to identify algorithms to be applied to the new medical logic. Most importantly, the illustrative embodiments learn the set and order of algorithms that should be applied for entity differentiation eliminating the need for manual defining of the set and order of the algorithms.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 8:
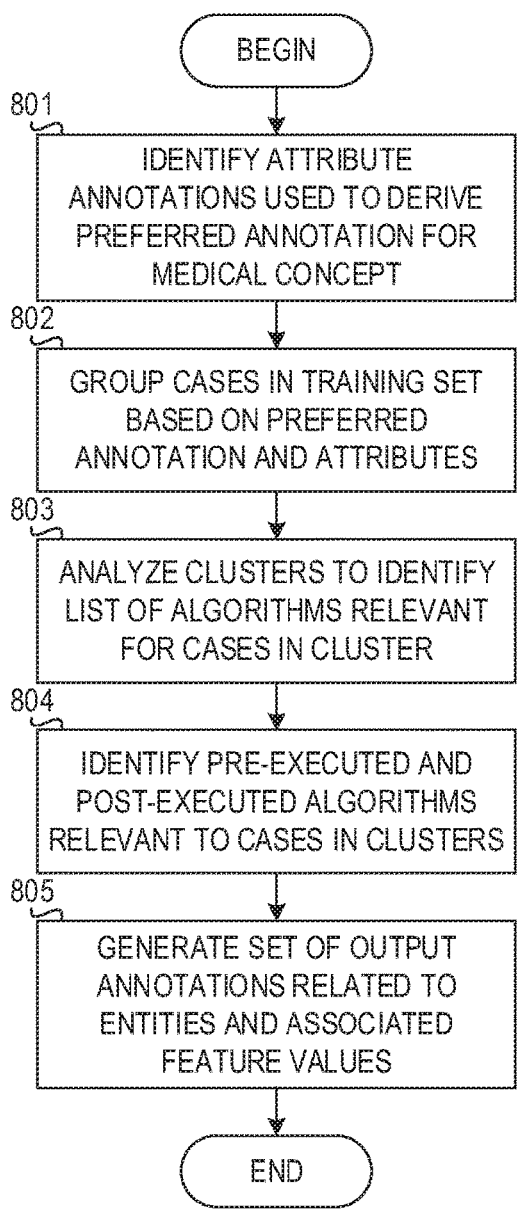
FIG. 8 is a flowchart outlining an example operation of an entity differentiation engine during a training phase of operation in accordance with one illustrative embodiment.

FIG. 8 is a flowchart outlining an example operation of an entity differentiation engine during a training phase of operation in accordance with one illustrative embodiment. As shown in FIG. 8, the operation starts by determining a set of annotations used to derive a most preferred annotation for a medical concept used to evaluate the medical concept as part of a performance of a cognitive operation, e.g., treatment recommendation (step 801). Machine learning is then performed to reverse engineer the evaluation of the medical concept to identify which algorithms are used for generating the most preferred annotation from the set of annotations. This machine learning may involve, for example, grouping cases (patient EMRs) in a training set of cases based on the preferred annotation and attributes associated with the various cases (step 802). Each cluster is then analyzed to identify a list of algorithms relevant for cases (patients) in the cluster to differentiate the preferred annotation (step 803). A set of pre-executed and post-executed algorithms relevant to the cases in the cluster are then identified (step 804). A set of output annotations related to entities and the associated feature values is obtained (step 805). The operation then terminates.

It should be appreciated that the algorithms can be defined as the building blocks that determine which attributes can be used with which heuristic. For example, knowing that a patient has undergone chemotherapy treatment can be represented by an attribute, such as chemotherapyUndergone=yes. This would be one of the important attributes that is used for determining a breast cancer treatment recommendation. An example algorithm that utilizes this attribute can be one that checks if the chemotherapy was within 6 months of a current time. Therefore, for patients that have a chemotherapyUndergone=yes attribute value, the dates of the chemotherapies are identified and are sorted. This algorithm will list all chemotherapy treatments that the patient has undergone based on the dates of the treatment. For those treatments that were within 6 months from the date of analysis (current time), a higher score is given than the other treatments for the given patient that are farther away from the current time. The fact that there is a breast tumor that is larger than 3 cm can be more important for breast cancer. Therefore, the algorithm that checks if there is a breast tumor that is larger than 3 cm will have a higher score than the algorithm that checks if the patient has undergone chemotherapy treatment within 6 months. Finding out this algorithms for the given disease (e.g. breast cancer) and the order in which they should be applied (e.g. tumor size in breast first, then the chemotherapy) is done using machine learning algorithms in the illustrative embodiments.

Figure 9:
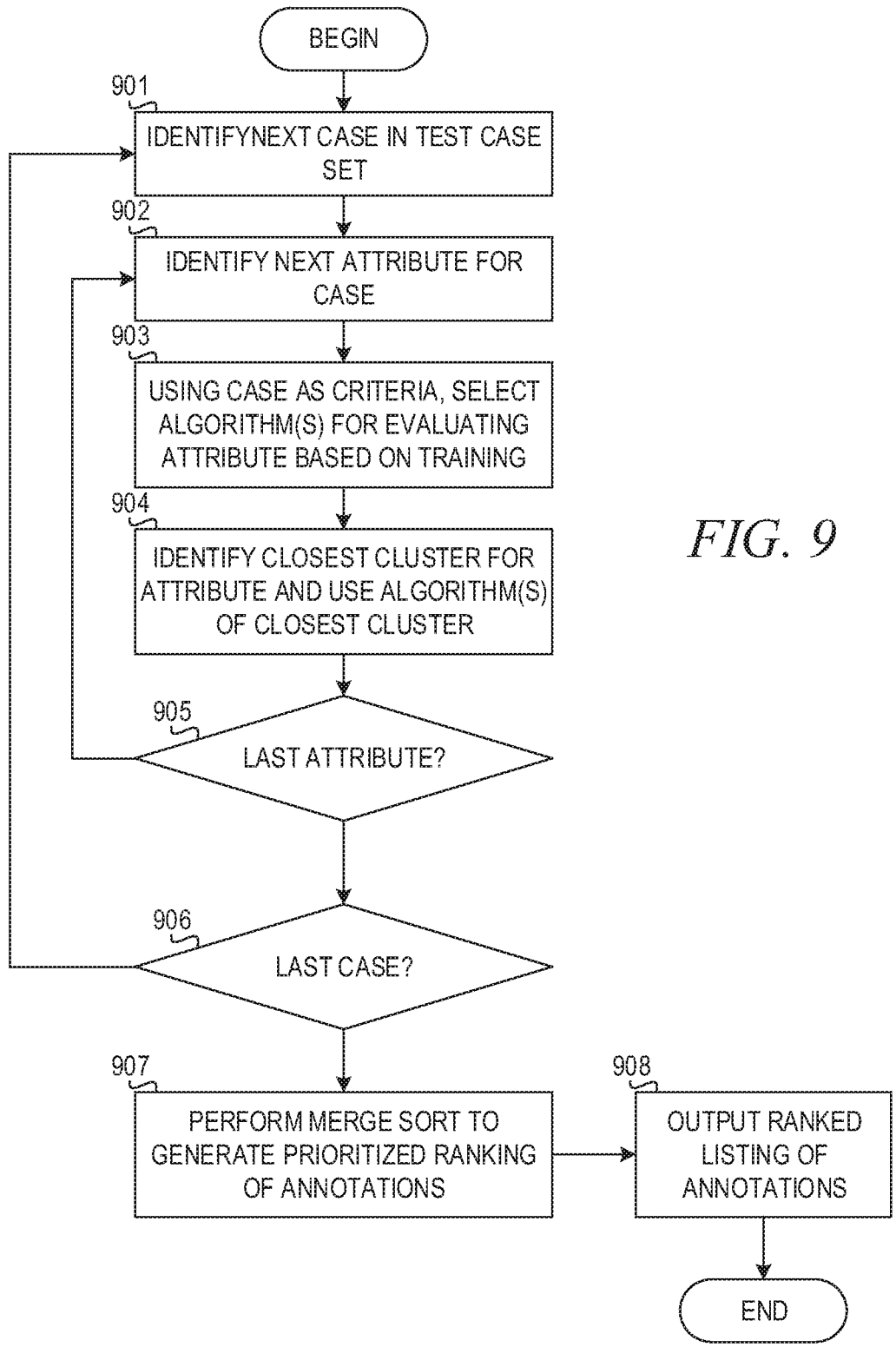
FIG. 9 is a flowchart outlining an example operation of an entity differentiation engine during a testing phase of operation in accordance with one illustrative embodiment.

FIG. 9 is a flowchart outlining an example operation of an entity differentiation engine during a testing phase of operation in accordance with one illustrative embodiment. As shown in FIG. 9, the operation starts by identifying a next case in a test set (step 901) and a next attribute for the case (step 902). For the attribute and case, e.g., patient electronic medical record, the most suitable algorithm, or set of algorithms, for evaluating the attribute is selected using the case as the criteria for the model learned during training. Each case, or patient electronic medical record, has different attribute values, therefore the differentiation step can result in different result. The model that is learned in training is the set of algorithms and their orders. For the given case, or patient electronic medical record, for each important attribute, the learned algorithms are applied (step 903). This may involve identifying a closest cluster for the attribute given all annotations in the case and using the algorithm(s) for the closest cluster (step 904). A determination is made as to whether this is the last attribute for the case (step 905). If not, the operation returns to step 903. If this is the last attribute, a determination is made as to whether this is the last case in the test case set (step 906). If not, the operation returns to step 901. If this is the last case in the test case set, then a merge sort is executed to percolate annotations that are higher priority to a top of a ranked list (step 907). The ranked list of annotations is then output (step 908) and the operation terminates.

Figure 10:
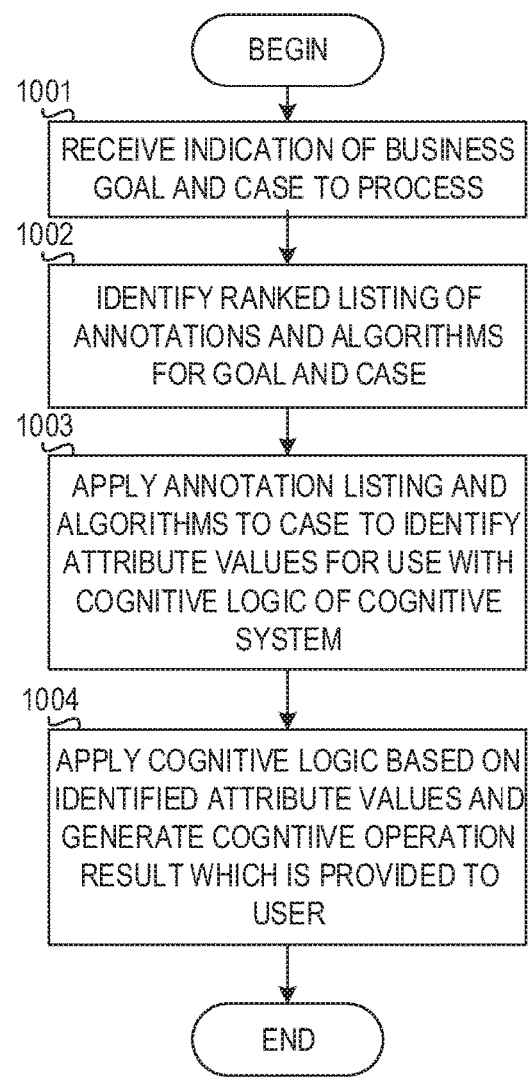
FIG. 10 is a flowchart outlining an example operation of an entity differentiation engine during a use phase of operation in accordance with one illustrative embodiment.

FIG. 10 is a flowchart outlining an example operation of an entity differentiation engine during a use phase of operation in accordance with one illustrative embodiment. As shown in FIG. 10, the operation starts by receiving an indication of a business goal and a case to be processed by the cognitive system (step 1001). Based on the business goal and the case, a corresponding ranked listing of annotations and set of algorithms used to identify the highest ranked annotation are retrieved from an entity differentiation knowledge source (step 1002). The annotations and set of algorithms are applied to the case to identify attribute values for use with the cognitive logic of the cognitive system (step 1003). The cognitive logic is applied based on the identified attribute values and a corresponding cognitive operation result is generated and provided to a user (step 1004). The operation then terminates.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a cognitive medical system and an entity differentiation component, the method comprising:

performing, by the entity differentiation component executing in the data processing system, machine learning on a training set of patient cases to learn, for each type of medical entity present in the patient cases, a corresponding ordered set of entity differentiation algorithms used to generate a correct value for the medical entity;

ingesting, by the cognitive medical system, a corpus of medical content, wherein the medical content comprises references to medical entities, and wherein ingesting the corpus comprises performing entity recognition on the medical content to identify the medical entities;

responsive to the cognitive medical system identifying, as part of the entity recognition, a medical entity having a plurality of annotations for a same medical entity attribute, determining, by the entity differentiation component executing in the data processing system, based on the learned correspondence of ordered sets of entity differentiation algorithms with each type of medical entity present in the patient cases, an ordered set of entity differentiation algorithms, corresponding to the medical entity, for differentiating medical entity attribute values;

running, by the entity differentiation component, the ordered set of entity differentiation algorithms, in order, on the plurality of annotations for the attribute to generate a ranked list of medical entity attribute values corresponding to the annotations in the plurality of annotations; and performing, by the cognitive medical system, a cognitive operation on the medical entity based on the ranked list of medical entity attribute values.

2. The method of claim 1, wherein performing machine learning on the training set of patient cases comprises for each medical concept in the training set of patient cases:

identifying an attribute annotation used to derive a preferred annotation for the medical entity;

clustering patient cases in the training set of patient cases according to the preferred annotation; and associating, with each cluster of patient cases in the training set of patient cases, a corresponding ordered set of entity differentiation algorithms based on the patient cases in the cluster and the preferred annotation.

3. The method of claim 2, wherein associating, with each cluster of patient cases in the training set of patient cases, the corresponding ordered set of entity differentiation algorithms comprises:

determining, for patient cases in the cluster, pre-execute algorithms relevant to the patient cases and post-execute algorithms relevant to the patient cases;

determining, for each patient case in the cluster, one or more output annotations related to medical entity;

determining, for each of the one or more output annotations, corresponding entity differentiation algorithms used to generate the one or more output annotations; and combining the pre-execute algorithms, the one or more output annotations, and the post-execute algorithms to formulate the corresponding ordered set of entity differentiation algorithms corresponding to the cluster.

4. The method of claim 1, wherein determining an ordered set of entity differentiation algorithms, corresponding to the medical entity, for differentiating medical entity attribute values comprises:

identifying a set of annotations used to derive a preferred annotation based on machine learning of the preferred annotation; and reverse engineering each annotation in the set of annotations to identify entity differentiation algorithms used to select the annotation to be part of the set of annotations.

5. The method of claim 1, wherein determining the ordered set of entity differentiation algorithms further comprises determining an implementation class and parameters associated with each entity differentiation algorithm in the ordered set of entity differentiation algorithms in the entity differentiation knowledge sources.

6. The method of claim 5, wherein running the ordered set of entity differentiation algorithms comprises running each of the ordered set of entity differentiation algorithms by calling its implementation class and passing the associated parameters.

7. The method in claim 1, wherein determining the ordered set of entity differentiation algorithms is based on a goal of the cognitive operation, wherein the goal comprises a treatment recommendation, adverse event analysis, or medical condition resolution.

8. The method of claim 1, wherein running the ordered set of entity differentiation algorithms comprises performing a merge sort based on results of running the ordered set of entity differentiation algorithms to generate the ranked list of medical entity attributes.

9. The method of claim 1, wherein the cognitive operation comprises generating a healthcare recommendation or performing clinical trials matching.

10. A computer program product comprising a computer readable storage medium having a computer readable program stored therein, wherein the computer readable program comprises instructions, which when executed on a processor of a computing device causes the computing device to implement a cognitive medical system and an entity differentiation component, wherein the computer readable program causes the computing device to:

perform, by the entity differentiation component, machine learning on a training set of patient cases to learn, for each type of medical entity present in the patient cases, a corresponding ordered set of entity differentiation algorithms used to generate a correct value for the medical entity;

ingest, by the cognitive medical system, a corpus of medical content, wherein the medical content comprises references to medical entities, and wherein ingesting the corpus comprises performing entity recognition on the medical content to identify the medical entities;

responsive to the cognitive medical system identifying, as part of the entity recognition, a medical entity having a plurality of annotations for a same medical entity attribute, determine by the entity differentiation component executing in the data processing system, based on the learned correspondence of ordered sets of entity differentiation algorithms with each type of medical entity present in the patient cases, an ordered set of entity differentiation algorithms, corresponding to the medical entity, for differentiating medical entity attribute values;

run, by the entity differentiation component, the ordered set of entity differentiation algorithms, in order, on the plurality of annotations for the attribute to generate a ranked list of medical entity attribute values corresponding to the annotations in the plurality of annotations; and perform, by the cognitive medical system, a cognitive operation on the medical entity based on the ranked list of medical entity attribute values.

11. The computer program product of claim 10, wherein performing machine learning on the training set of patient cases comprises for each medical concept in the training set of patient cases:

identifying an attribute annotation used to derive a preferred annotation for the medical entity;

clustering patient cases in the training set of patient cases according to the preferred annotation; and associating, with each cluster of patient cases in the training set of patient cases, a corresponding ordered set of entity differentiation algorithms based on the patient cases in the cluster and the preferred annotation.

12. The computer program product of claim 11, wherein associating, with each cluster of patient cases in the training set of patient cases, the corresponding ordered set of entity differentiation algorithms comprises:

determining, for patient cases in the cluster, pre-execute algorithms relevant to the patient cases and post-execute algorithms relevant to the patient cases;

determining, for each patient case in the cluster, one or more output annotations related to medical entity;

determining, for each of the one or more output annotations, corresponding entity differentiation algorithms used to generate the one or more output annotations; and combining the pre-execute algorithms, the one or more output annotations, and the post-execute algorithms to formulate the corresponding ordered set of entity differentiation algorithms corresponding to the cluster.

13. The computer program product of claim 10, wherein determining an ordered set of entity differentiation algorithms, corresponding to the medical entity, for differentiating medical entity attribute values comprises:

identifying a set of annotations used to derive a preferred annotation based on machine learning of the preferred annotation; and reverse engineering each annotation in the set of annotations to identify entity differentiation algorithms used to select the annotation to be part of the set of annotations.

14. The computer program product of claim 10, wherein determining the ordered set of entity differentiation algorithms further comprises determining an implementation class and parameters associated with each entity differentiation algorithm in the ordered set of entity differentiation algorithms in the entity differentiation knowledge sources.

15. The computer program product of claim 14, wherein running the ordered set of entity differentiation algorithms comprises running each of the ordered set of entity differentiation algorithms by calling its implementation class and passing the associated parameters.

16. The computer program product in claim 10, wherein determining the ordered set of entity differentiation algorithms is based on a goal of the cognitive operation, wherein the goal comprises a treatment recommendation, adverse event analysis, or medical condition resolution.

17. The computer program product of claim 10, wherein running the ordered set of entity differentiation algorithms comprises performing a merge sort based on results of running the ordered set of entity differentiation algorithms to generate the ranked list of medical entity attributes.

18. A computing device comprising:

at least one processor; and at least one memory coupled to the at least one processor, wherein the at least one memory comprises instructions, which when executed on the at least one processor of the computing device causes the computing device to implement a cognitive medical system and an entity differentiation component, wherein the instructions cause the computing device to:

perform, by the entity differentiation component, machine learning on a training set of patient cases to learn, for each type of medical entity present in the patient cases, a corresponding ordered set of entity differentiation algorithms used to generate a correct value for the medical entity;

ingest, by the cognitive medical system, a corpus of medical content, wherein the medical content comprises references to medical entities, and wherein ingesting the corpus comprises performing entity recognition on the medical content to identify the medical entities;

responsive to the cognitive medical system identifying, as part of the entity recognition, a medical entity having a plurality of annotations for a same medical entity attribute, determine by the entity differentiation component executing in the data processing system, based on the learned correspondence of ordered sets of entity differentiation algorithms with each type of medical entity present in the patient cases, an ordered set of entity differentiation algorithms, corresponding to the medical entity, for differentiating medical entity attribute values;

run, by the entity differentiation component, the ordered set of entity differentiation algorithms, in order, on the plurality of annotations for the attribute to generate a ranked list of medical entity attribute values corresponding to the annotations in the plurality of annotations; and perform, by the cognitive medical system, a cognitive operation on the medical entity based on the ranked list of medical entity attribute values.

* * * * *